(12) United States Patent
Cho et al.

(10) Patent No.: US 10,004,453 B2
(45) Date of Patent: Jun. 26, 2018

(54) NEURAL PROBE STRUCTURE COMPRISING COVER ELEMENT WHERE FLUID DELIVERY CHANNEL IS FORMED

(71) Applicant: KOREA INSTITUTE OF SCIENCE AND TECHNOLOGY, Seoul (KR)

(72) Inventors: Il-Joo Cho, Seoul (KR); Eui Sung Yoon, Seoul (KR); Hyogeun Shin, Seoul (KR); Uikyu Chae, Seoul (KR); Hyunjoo Jenny Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 157 days.

(21) Appl. No.: 15/250,469

(22) Filed: Aug. 29, 2016

(65) Prior Publication Data

US 2017/0065764 A1   Mar. 9, 2017

(30) Foreign Application Priority Data

Sep. 3, 2015  (KR) ........................ 10-2015-0124796

(51) Int. Cl.
*A61M 5/32*   (2006.01)
*A61B 5/00*   (2006.01)
(Continued)

(52) U.S. Cl.
CPC ........ *A61B 5/4848* (2013.01); *A61B 5/04001* (2013.01); *A61B 5/6848* (2013.01);
(Continued)

(58) Field of Classification Search
CPC .............. A61B 5/04001; A61B 5/4848; A61B 2562/028; A61M 39/105; A61M 5/1407; A61M 5/158; B01L 2300/0883
See application file for complete search history.

(56) References Cited

U.S. PATENT DOCUMENTS 5,989,445 A  *  11/1999  Wise ....................... A61M 5/32
                                                         216/2
5,992,769 A     11/1999  Wise et al.
(Continued)

FOREIGN PATENT DOCUMENTS

KR       10-1250794 B1    4/2013
KR     10-2015-0088648 A  8/2015

OTHER PUBLICATIONS

Rohatgi, Pratik, et al. "In vivo performance of a microelectrode neural probe with integrated drug delivery." Neurosurgical focus 27.1 (2009): E8.

*Primary Examiner* — Rebecca E Eisenberg
(74) *Attorney, Agent, or Firm* — NSIP Law (57) ABSTRACT

A neural probe structure has a probe having a microfluidic channel. The probe is inserted into an inside of a subject. A body to which the probe is fixed has a fluid entrance communicating with the microfluidic channel. A cover element is fixed to the body to cover the fluid entrance. The cover element has a connecting opening to which an external conduit is connected, and a fluid delivery channel extending such that the connecting opening and the fluid entrance are in fluid communication. A fluid fed from the external conduit flows along the fluid delivery channel, goes into the fluid entrance, and is delivered to the subject through the microfluidic channel.

17 Claims, 8 Drawing Sheets

(51) Int. Cl.
    *A61B 5/04*     (2006.01)
    *A61M 5/158*    (2006.01)
    *A61M 39/10*    (2006.01)

(52) U.S. Cl.
    CPC .......... *A61M 5/158* (2013.01); *A61M 39/105*
        (2013.01); *A61B 2562/028* (2013.01); ***A61M
                                  2210/0693*** (2013.01)

(56) References Cited

U.S. PATENT DOCUMENTS

| | | | | |
|---|---|---|---|---|
| 6,908,594 | B1* | 6/2005 | Schaevitz | B01L 3/5025 |
| | | | | 204/451 |
| 7,524,464 | B2* | 4/2009 | Ahn | A61B 5/14532 |
| | | | | 422/168 |
| 2005/0047969 | A1* | 3/2005 | Zhao | B01L 3/0268 |
| | | | | 422/503 |
| 2005/0211559 | A1* | 9/2005 | Kayyem | B01L 3/5027 |
| | | | | 204/601 |
| 2013/0256138 | A1* | 10/2013 | Heideman | B01L 3/502707 |
| | | | | 204/601 |
| 2013/0345780 | A1* | 12/2013 | Tabada | A61N 1/04 |
| | | | | 607/115 |
| 2015/0208963 | A1 | 7/2015 | Lee et al. | |

\* cited by examiner

NEURAL PROBE STRUCTURE COMPRISING COVER ELEMENT WHERE FLUID DELIVERY CHANNEL IS FORMED

CROSS-REFERENCE TO RELATED APPLICATION

This application claims priority to Korean Patent Application No. 2015-0124796, filed on Sep. 3, 2015, and all the benefits accruing therefrom under 35 U.S.C. § 119, the contents of which in its entirety are herein incorporated by reference.

BACKGROUND

1. Field

The present disclosure relates to a neural probe structure, and more particularly, to a neural probe structure comprising a cover element where a fluid delivery channel is formed, for delivering a fluid supplied from the exterior to a probe.

2. Description of the Related Art

A microfluidic channel is one of key structures of not only a micro fluid chip widely used in the biomedical field but also a Micro Electro Mechanical Systems (MEMS) neural probe that is used to treat brain diseases and define brain activity.

For example, when injecting a small amount of tracing drugs into the brain of an animal to study functional brain circuits, a microneedle is used, and the microneedle needs a microfluidic channel to deliver the drugs well.

Also, to test drugs used to treat brain diseases or disorders, drug delivery to the brain is required, but because intravenous administration is impossible due to the Blood Brain Barrier (BBB), the drugs are administered using a microneedle.

Accordingly, many fabrication methods including bonding a separately fabricated microfluidic channel to an MEMS probe have been introduced.

In using the probe including the microfluidic channel, when connecting an external conduit to the probe using a mechanical connector, a dead volume between the external conduit and the probe significantly increases. Thus, when there is a change in fluid or concentration to feed, the dead volume causes a delay in the time it takes to show the impact of the change, making it impossible to accurately subjects' reaction.

Particularly, when a very small amount of drugs are fed, the problem with delay in drug change becomes severer, therefore, in bonding the external conduit to the probe, a structure for minimizing the dead volume is required.

SUMMARY

The present disclosure is directed to providing a neural probe structure comprising a cover element for delivering a fluid supplied from an external conduit to a probe.

According to an embodiment of the present disclosure, a neural probe structure includes a probe having a microfluidic channel, wherein the probe is inserted into an inside of a subject, a body to which the probe is fixed, the body having a fluid entrance communicating with the microfluidic channel, and a cover element fixed to the body to cover the fluid entrance, wherein the cover element comprises a connecting opening to which an external conduit is connected, a delivery opening placed above and aligned with the fluid entrance, and a fluid delivery channel extending such that the connecting opening and the delivery opening are in fluid communication, and a fluid fed from the external conduit flows along the fluid delivery channel, goes into the fluid entrance, and is delivered to the subject through the microfluidic channel.

According to an embodiment of the present disclosure, the cover element may include a plurality of connecting openings to which a plurality of external conduits is connected.

According to an embodiment of the present disclosure, the fluid delivery channel may include a discharge pipeline extending from the fluid entrance, and a plurality of feed pipelines branching from the discharge pipeline and extending in communication with each of the plurality of connecting openings.

According to an embodiment of the present disclosure, the feed pipeline may be formed to have a curved channel.

According to an embodiment of the present disclosure, the plurality of feed pipelines may have a same cross section perpendicular to a flow direction of the fluid and a same length.

According to an embodiment of the present disclosure, a plurality of protrusions may be formed on an inner wall of the discharge pipeline.

According to an embodiment of the present disclosure, different fluids may be supplied from each of the plurality of external conduits, and a blending ratio of fluids discharged from the probe may be adjusted by adjusting an amount of each fluid supplied.

According to an embodiment of the present disclosure, a width of the delivery opening may be smaller than a width of the fluid entrance.

According to an embodiment of the present disclosure, the fluid delivery channel may be formed by covering a groove formed in the cover element with the body.

According to an embodiment of the present disclosure, the body may be made of silicon, and the cover element may be made of polydimethylsiloxane (PDMS).

According to an embodiment of the present disclosure, the body and the cover element may be bonded by plasma bonding.

According to an embodiment of the present disclosure, the neural probe structure may further include a flow rate measuring sensor at an entrance of the microfluidic channel.

According to an embodiment of the present disclosure, the cover element may be configured such that the external conduit is detachably fixed to the cover element.

According to an embodiment of the present disclosure, the probe may have an electrode to measure a neural signal emitted in response to the drug.

DETAILED DESCRIPTION

Hereinafter, a neural probe structure according to an embodiment of the present disclosure will be described with reference to the accompanying drawings.

Figure 1:
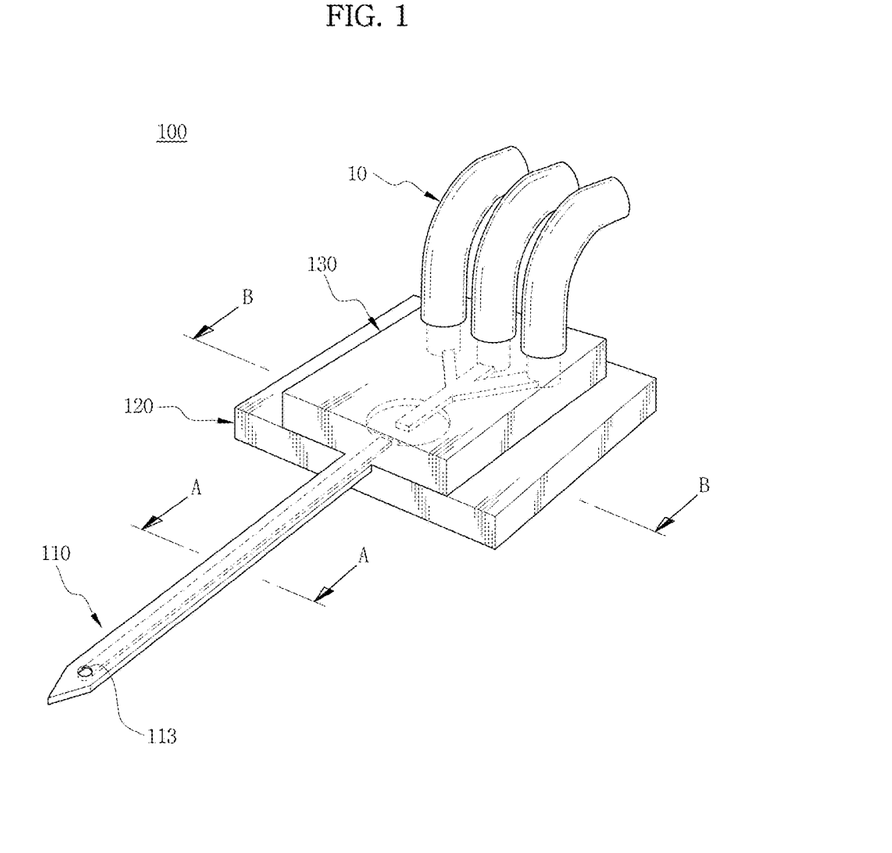
FIG. 1 is an outline perspective view of a neural probe structure according to an embodiment of the present disclosure.
Figure 2:
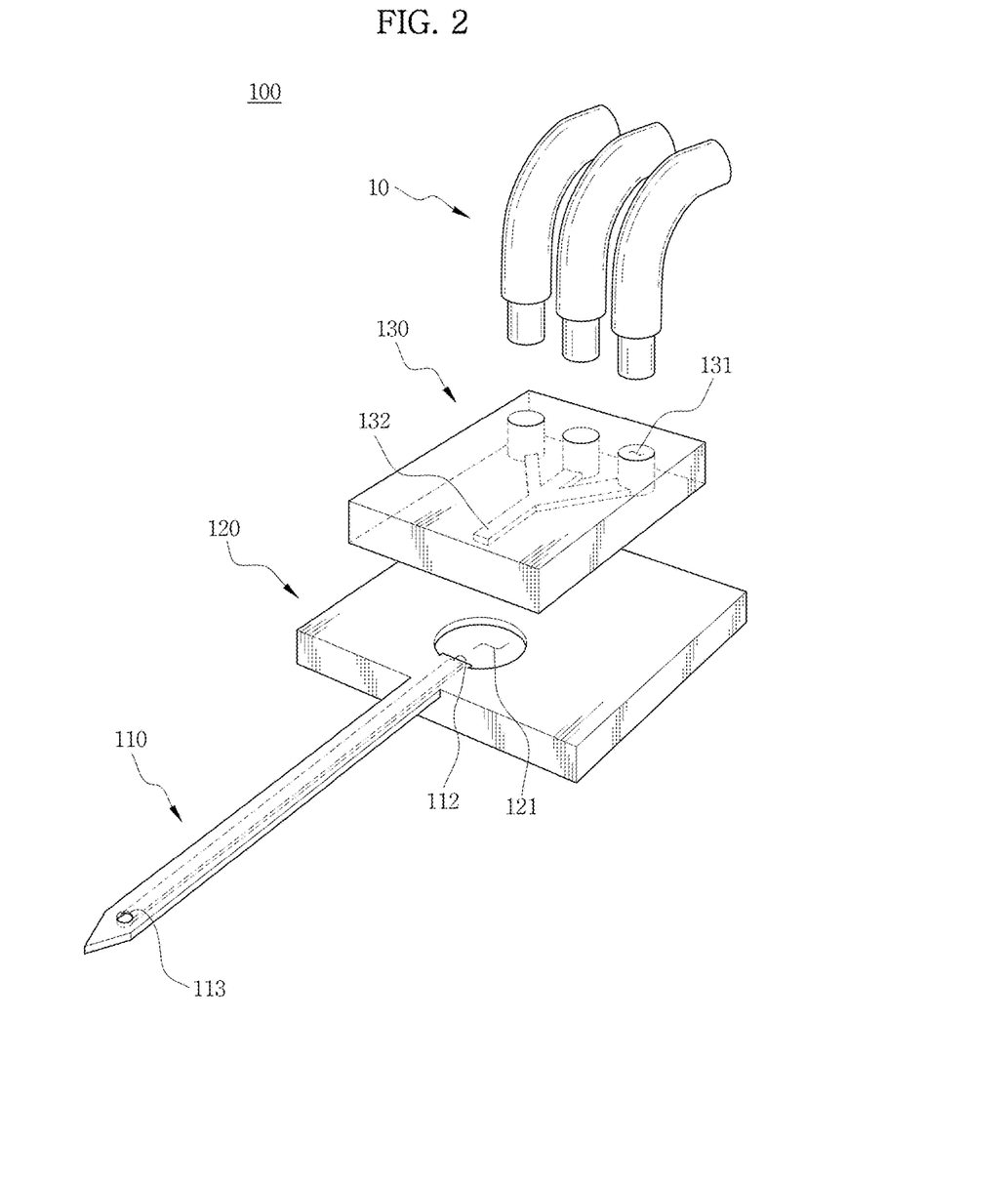
FIG. 2 is an outline exploded perspective view of the neural probe structure of FIG. 1.

Referring to FIGS. 1 and 2, a neural probe structure 100 according to an embodiment of the present disclosure includes a probe 110, a body 120, and a cover element 130.

The probe 110 is inserted into the inside of a subject such as a mouse. Preferably, a front end part of the probe 110 is elongated to minimize damage of an insertion site when inserted, and is sharp to allow easy insertion into the body of the subject.

The probe 110 is fixed to the body 120. The probe 110 is formed in such a shape that the rear end part is fixed to one side of the body 120 and the front end part protrudes from the body 120. The probe 110 may be integrally formed with the body 120. Also, the probe 110 and the body 120 may be formed on a wafer made of silicon.

The probe 110 has a microfluidic channel through which a fluid flows. The microfluidic channel is in fluid communication from a channel entrance 112 of the probe 110 to a channel exit 113. The microfluidic channel may pass through the inside of the probe 110.

Referring to 3A through 3E, a probe body 114 can be produced using the a DRIE (deep reactive-ion etching) process. The microfluidic channel can be configured in such a manner that a cover glass 115 covers upper side of the probe body 114 having a recessed groove.

Figure 3A:
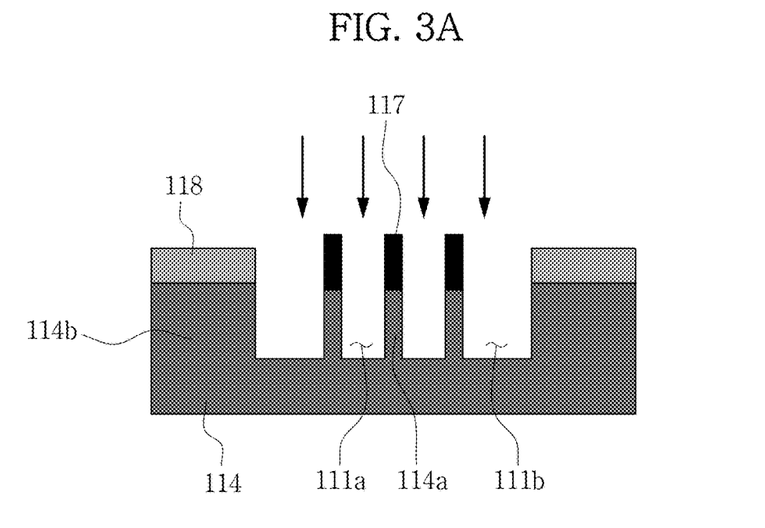
FIGS. 3A through 3E are a side cross-sectional view of the neural probe structure of FIG. 1, taken along the line A-A.

At first, a first mask 117 is coated on top of a channel wall 114a and a second mask 118 is coated on top of an anchor wall 114b. In the processing of a DRIE upon the application of the masks, a portion of the probe body between each wall 114a, 114b will be etched in constant depth and will form grooves 111a, 111b as shown in FIG. 3A, Since a channel groove 111a between the channel walls 114a forms a microfluidic channel, the channel groove 111a can have a narrower width than that of an anchor groove 111b between the anchor wall 114b and the channel wall 114a. Considering different widths of the grooves, it is preferable to coat the masks 117, 118 suitably.

Figure 3B:
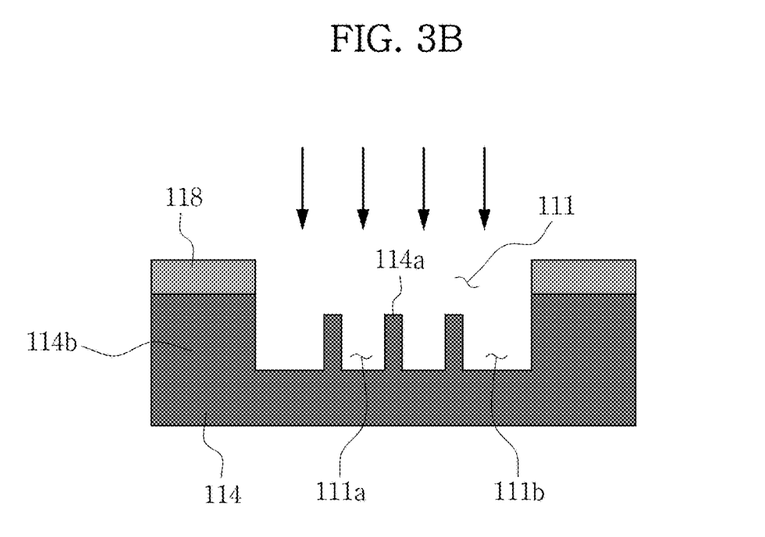

Subsequently, as shown in FIG. 3B, the second process of a DRIE is preceded after removing of the first mask 117. Through the second process of a DRIE, the channel wall 114a and the grooves 111a, 111b are etched deeply. Therefore, the heights of the channel wall 114a decrease lower than the anchor wall 114b.

Figure 3C:
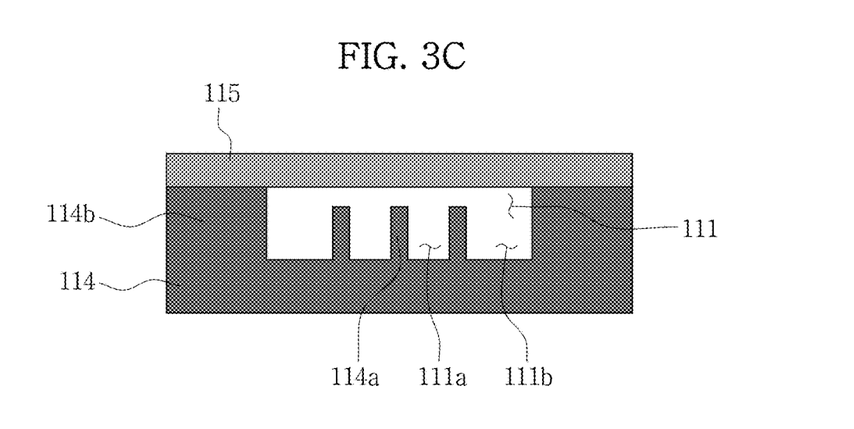

Next, a cover glass 115 is joined to an upper side of the probe body 114, as shown in FIG. 3C. The probe body 114 and the cover glass 115 can be strongly joined by an anodic bonding caused by voltages.

Figure 3D:
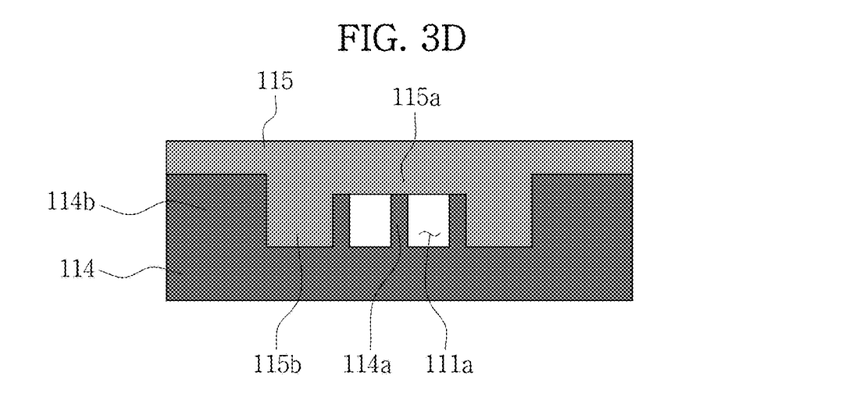

The cover glass 115 fixed to the probe body 114 is heated on the higher temperature of the melting point of glasses but lower than the melting point of silicones. Due to heating, the melted cover glass 115 will flow into the groove 111 as shown in FIG. 3D.

The melted cover glass 115 then flows into the anchor groove 111b, which is relatively wider than the channel groove, and completely fills the anchor groove 111b. However, at the channel groove 111a, which is relatively smaller than the anchor groove, the melted cover glass 115 is blocked by the channel wall 114a and cannot flow into the channel groove 111a. Therefore, the channel portion 115a of the cover glass 115 is supported by the channel wall 114a and covers an upper opening. The anchor portion 115b of the cover glass 115 is completely inserted into the anchor groove 111b and fixes the cover glass 115 to the probe body 114.

Figure 3E:
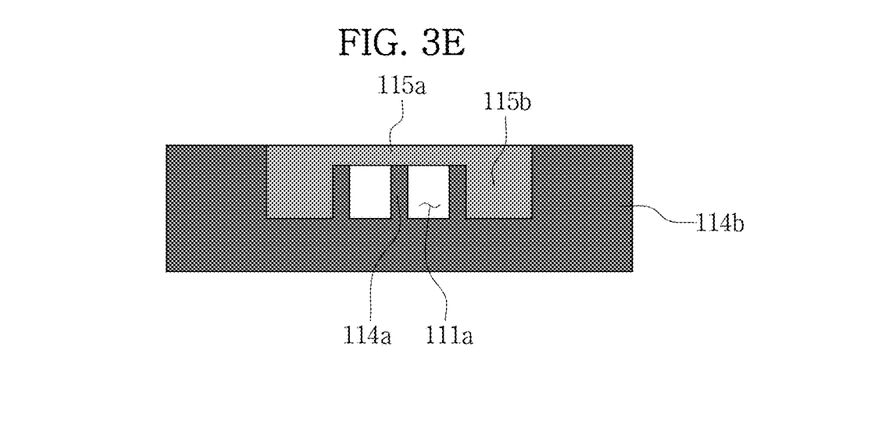

As the cover glass 115 hardens sufficiently, the upper part is polished for flattening the surface of the upper part of the cover glass 115 and the probe body 114 as shown in FIG. 3E. In other words, the outer surface of the above cover glass 115 and the outer surface of the probe body 114, where the cover glass 115 is inserted, are placed on the same plane. Thereby, this could minimize the total thickness of the probe 110 and prevent damages to the subject when the probe 110 is inserted into the body of the subject.

In this case, the anchor portion of the cover glass 115 that filled in the anchor groove 111b increases the fixing strength and prevents loss of a portion of the cover glass 115 in the groove 111 during the process of polishing the upper portion of the cover glass 115.

Finally, cutting the probe body 114 into the proper shape, the probe 110 can be formed as shown in FIGS. 1 and 2.

The microfluidic channel communicates with a fluid entrance 121 formed in the body 120. The microfluidic channel may extend to the body 120. Thereby, the fluid fed from the fluid entrance 121 to the channel entrance 112 may be delivered to the channel exit 113 at the front end part of the probe 110 through the microfluidic channel.

The probe 110 may further include an electrode array (not shown) to collect reaction signals from the subject. The reaction signals collected by the electrode array may be transmitted to a printed circuit board (PCB) (not shown) placed on the body 120 along an electrical wire (not shown). Through this, it is possible to know the reaction occurring from the subject during drug delivery by the neural probe structure 100.

Figure 4:
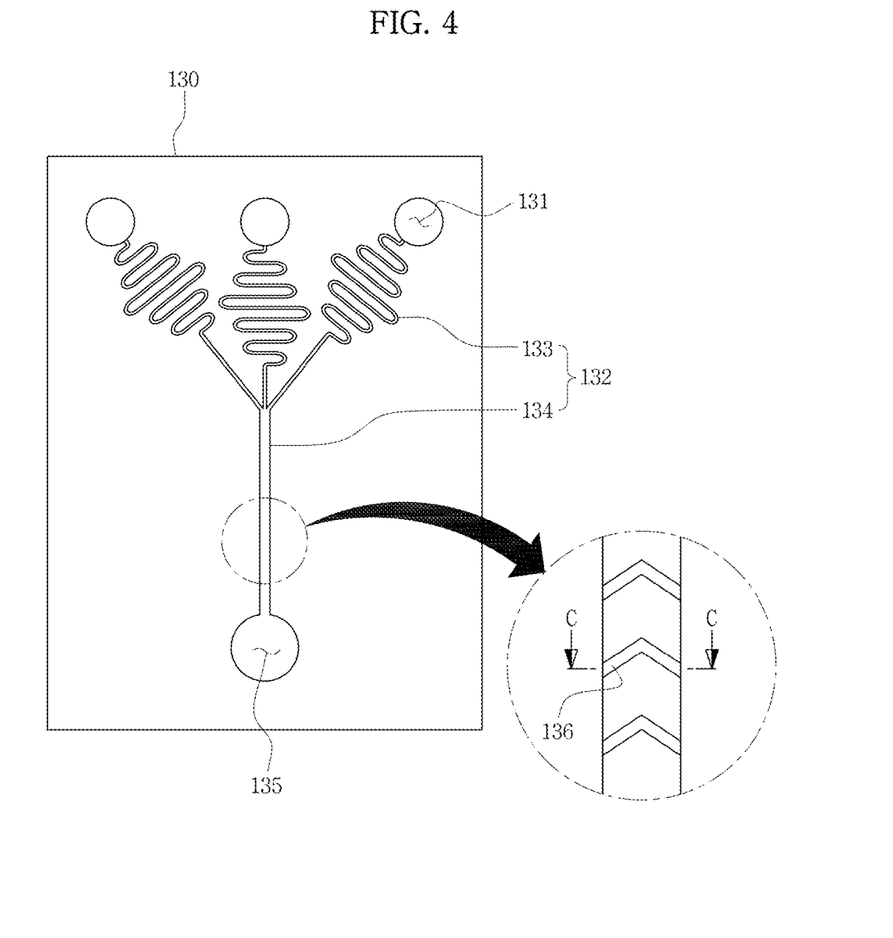
FIG. 4 is an outline bottom view of a cover element of the neural probe structure of FIG. 1.

Referring to FIG. 4, the cover element 130 includes a connecting opening 131 formed to connect to an external conduit 10. The external conduit 10 may be detachably fixed in the connecting opening 131. The cover element 130 is preferably made of a soft material to establish a close connection of the external conduit 10 to the connecting opening 131, thereby preventing fluid leaks and air inflow.

On the other hand, the cover element 130 may include a plurality of connecting openings 131 to which a plurality of external conduits 10 is connected. That is, the plurality of external conduits 10 may be individually connected to each of the connecting openings 131. Thereby, different fluids can be supplied from each external conduit 10. Also, each external conduit 10 can be individually controlled.

Also, the cover element 130 includes a fluid delivery channel 132 which extends from the connecting opening 131. The fluid delivery channel 132 may be formed such that it passes through the inside of the cover element 130, while the fluid delivery channel 132 is preferably formed by covering a recessed groove formed on the lower surface with the body 120 because it is easy to fabricate.

As the cover element 130 is bonded to the body 120, the upper surface of the body 120 comes into contact with the lower surface of the cover element 130. In this instance, the upper surface of the body 120 covers the open lower surface of the fluid delivery channel 132. Thus, the fluid delivery channel 132 has no region open to the exterior, and the fluid may be delivered from the connecting opening 131 to a delivery opening 135 through the fluid delivery channel 132.

The fluid delivery channel 132 may include a plurality of feed pipelines 133 which extend from each of the plurality of connecting openings 131 to which the plurality of external conduits 10 is connected. Fluid supplied to the connecting opening 131 is fed into the feed pipeline 133 connected to the connecting opening 131.

Also, the fluid delivery channel 132 may include a discharge pipeline 134 which communicates with each of the plurality of feed pipelines 133 and extends to the fluid entrance 121. The plurality of feed pipelines 133 may be connected to one discharge pipeline 134. Thereby, fluids moving through each feed pipeline 133 are gathered and blended in the discharge pipeline 134.

That is, the fluid delivery channel 132 may include the discharge pipeline 134 which extends from the fluid entrance 121, and the plurality of feed pipelines 133 which branches from the discharge pipeline 134 and extends in communication with the plurality of connecting openings 131 respectively.

On the other hand, the feed pipeline 133 may provide fluid resistance to the external conduit 10 and the discharge pipeline 134 in proportion to the length. Thereby, by adjusting the pressure of fluids supplied through the external conduit 10, an amount of fluids injected through each connecting opening 131 can be accurately controlled.

In this instance, the feed pipeline 133 may be formed to have a curved channel in a zigzag shape as shown. Thus, even in the limited space, the longer feed pipeline 133 can be formed, and the feed pipeline 133 can provide an increased magnitude of fluid resistance. On the other hand, the feed pipeline 133 is not limited to the illustration, and it may have various shapes taking into account the space in the cover element 130 and the length of the feed pipeline 133 as a function of a preset fluid resistance.

On the other hand, the feed pipelines 133 may be formed with the same cross section perpendicular to the flow direction of fluid and the same length. Thereby, as each feed pipeline 133 has the same fluid resistance, even though a larger amount of fluids are supplied from one external conduit 10 than other external conduit 10, the pressure at the region where each feed pipeline 133 meets the discharge pipeline 134 is uniformly maintained, thereby preventing a fluid backdraft from the discharge pipeline 134 to the feed pipeline 133.

On the other hand, a plurality of protrusions 136 may be formed on the inner wall at the side of the cover element 130 defining the discharge pipeline 134. By the protrusion 136, turbulence is created in fluid passing through the discharge pipeline 134, to allow uniform blend of fluids. Although the shape of the protrusion 136 is such that a sharp part in bent shape faces the opposite direction to the flow direction as shown, other known shapes may be employed. Also, the pattern interval of the protrusion 136 may be appropriately selected in consideration of the width and length of the discharge pipeline 134.

On the other hand, although the discharge pipeline 134 is shown as a straight line shape, the discharge pipeline 134 is not limited thereto and may be curved or formed in a zigzag shape by as much as a section length needed to uniformly blend fluids by the protrusion 136.

Figure 5:
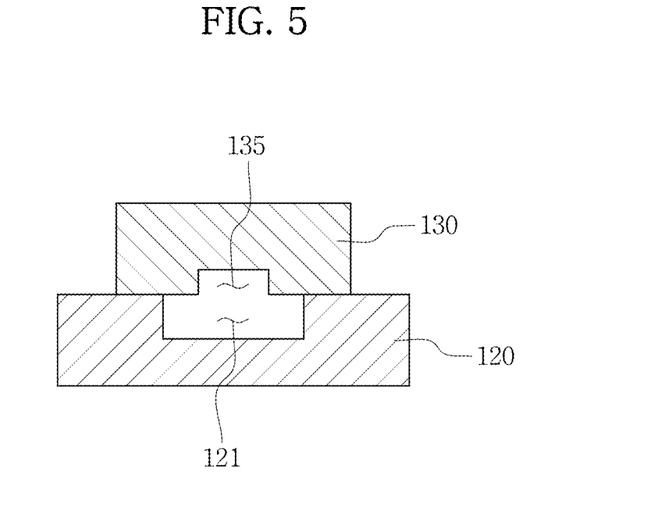
FIG. 5 is a side cross-sectional view of the neural probe structure of FIG. 1, taken along the line B-B.

Referring to FIG. 5, the cover element 130 described in the foregoing is fixed to the body 120 such that the delivery opening 135 is disposed on the fluid entrance 121 of the body 120. As the delivery opening 135 and the fluid entrance 121 are aligned, fluid passing through the fluid delivery channel 132 may move from the delivery opening 135 to the fluid entrance 121.

In this instance, the width of the delivery opening 135 may be smaller than the width of the fluid entrance 121.

Thereby, the delivery opening 135 may be aligned on the fluid entrance 121 more easily.

An internal space formed by the fluid entrance 121 and the delivery opening 135 is a space communicating with the discharge pipeline 134 and the microfluidic channel. When the body 120 and the cover element 130 are bonded, as the fluid entrance 121 and the delivery opening 135 increases in size, it is easy to align the fluid entrance 121 with the delivery opening 135, but when the size is larger than necessary, a large amount of fluids are trapped in the internal space formed by the fluid entrance 121 and the delivery opening 135. In the case where an amount of fluid trapped is large, when there is a change in fluid fed into each external conduit 10, the time it takes to discharge the changed fluid through the channel exit 113 increases. In the respect that delay in fluid change can be minimized, it is preferable to minimize the space formed by the fluid entrance 121 and the delivery opening 135.

In sum, when fluids are supplied from the exterior to the neural probe structure 100 through the external conduit 10, the fluids go into the connecting opening 131 of the cover element 130, flow along each feed pipeline 133 of the fluid delivery channel 132, and are gathered in the discharge pipeline 134 through which the fluids are uniformly blended, then are transferred from the delivery opening 135 to the fluid entrance 121 of the body 120, and subsequently are introduced into the channel entrance 112 and exit the channel exit 113 through the microfluidic channel, so fluid delivery to the subject is accomplished.

On the other hand, the body 120 may be made of silicon, and the cover element 130 may be made of polydimethylsiloxane (PDMS). In this instance, the body 120 and the cover element 130 may be firmly bonded by plasma bonding. Thereby, even though each structure in the body 120 and the cover element 130 is formed in microsize, leaks of fluid between the body 120 and the cover element 130 may be prevented. Particularly, as the fluid delivery channel 132 and the delivery opening 135 form a space for fluid movement when they come into contact with the body 120, firmer bonding of the body 120 and the cover element 130 is desirable.

On the other hand, because the body 120 and the cover element 130 themselves are bonded by plasma bonding without a separate mechanical connector, even though the fluid entrance 121 and the delivery opening 135 are formed in a relatively smaller size than earlier, they can be accurately aligned. Thereby, it is possible to minimize a space in which fluid is trapped and immediately change the flow rate and concentration by the fluid control.

Hereinafter, a process of fabricating the foresaid cover element 130 is described with reference to FIGS. 6A through 6E.

Figure 6A:
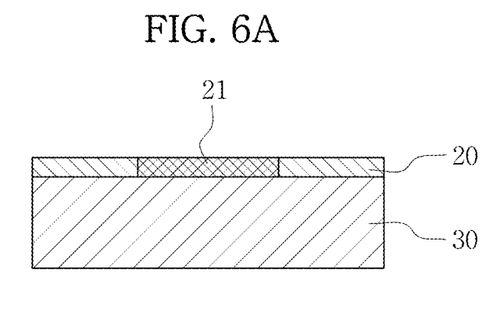
FIGS. 6A through 6E are outline side cross-sectional view showing a process of fabricating a cover element of the neural probe structure of FIG. 1, taken along the line C-C of FIG. 4.

Referring to FIG. 6A, first, a mold element 20 is coated on a support for molding 30. For the mold element 20, SU-8 may be used. A desired region of the coated mold element 20 is cured by light irradiation to form a mold 21.

Figure 6B:
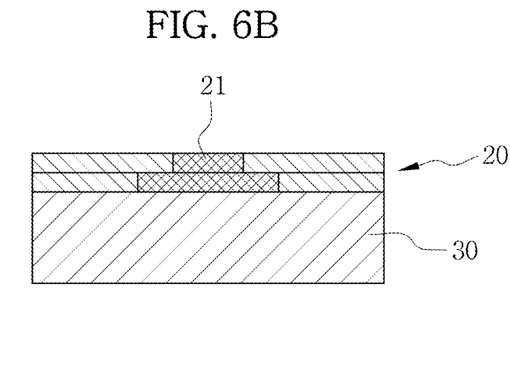

Subsequently, as shown in FIG. 6B, a one more layer of mold element 20 is coated on a layer of the mold element 20 and the mold 21 of FIG. 6A. The newly coated mold element 20 is cured by light irradiation to additionally form the mold 21.

Figure 6C:
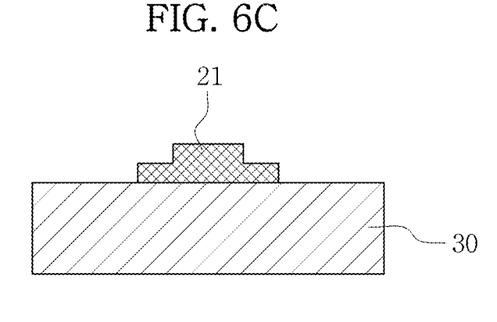

Subsequently, as shown in FIG. 6C, an uncured mold element 20 is removed, only leaving the mold 21 on the body 120.

Figure 6D:
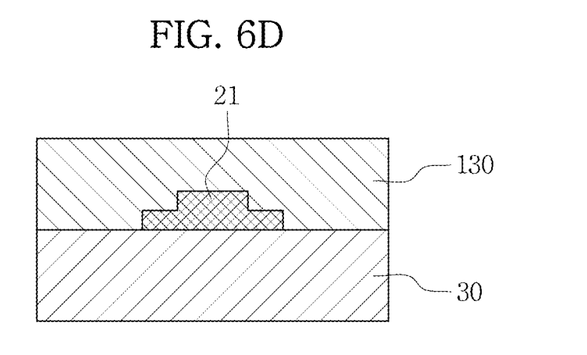

After a cast (not shown) is placed around the body 120 having gone through the above process, the cover element 130 is formed on the support for molding 30 and the mold 21 as shown in FIG. 6D. The cover element 130 is cured to conform to the shape of the mold 21 and the cast.

Figure 6E:
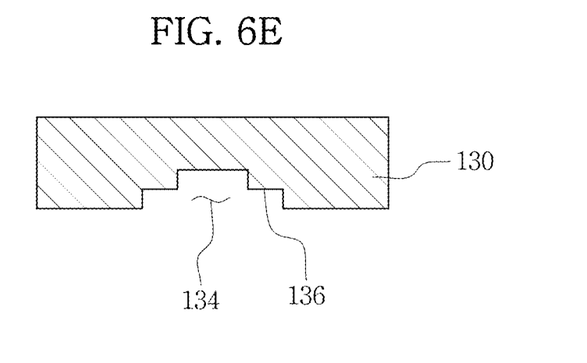

After the curing of the cover element 130 is completed, the mold 21 and the support for molding 30 are removed from the cover element 130 as shown in FIG. 6E.

By forming the multi-step mold 21 in this way, a multi-step concave structure can be formed on the lower surface of the cover element 130. Although FIG. 6E shows the discharge pipeline 134 having a relative larger depth and the protrusion 136 having a relatively smaller depth, the feed pipeline 133 may be formed in the foresaid manner.

In fabricating the cover element 130, the thickness and width of each layer that makes up the mold 21 may be variously set depending on the thickness and width of the feed pipeline 133, the discharge pipeline 134, and the protrusion 136.

On the other hand, the process of fabricating the cover element 130 is provided for illustration purposes, and the cover element 130 may be fabricated by a variety of known fabrication methods.

On the other hand, the neural probe structure 100 according to an embodiment of the present disclosure may further include a flow rate measuring sensor (not shown). The flow rate measuring sensor may be disposed at the channel entrance 112 to measure an amount of fluid fed through the microfluidic channel. The flow rate measuring sensor may be disposed at other locations.

The neural probe structure 100 according to an embodiment of the present disclosure as described in the foregoing may be inserted into part of the nerves to test, and used to apply a stimulus and collect reaction.

First, the probe 110 is inserted into a test site of a subject, such as the subject's brain. Upon insertion of the probe 110, drugs of desired type and concentration are injected by adjusting the pressure applied to each external conduit 10. Each drug fed through the plurality of external conduits 10 flows along the fluid delivery channel 132 and is introduced into the fluid entrance 121. Each drug is blended through the fluid delivery channel 132. The blend of drugs goes into the channel entrance 112 and exits the channel exit 113 through the microfluidic channel, then the drug delivery to the subject is accomplished.

The delivered drug stimulates the nerves of the subject. Reaction signals generated from the nerves of the subject in response to the drug are collected by the electrode array integrated on the probe 110. Signal information collected by the electrode array is transmitted to the PCB through the electrical wire and sent to an external computer (not shown). The received reaction signal information may be used to analyze the neural activity of the subject.

Although the embodiments of the present disclosure have been hereinabove described in further detail with reference to the accompanying drawings, the present disclosure is not necessarily limited to these embodiments, and modifications may be made to the embodiments in various forms without departing from the technical spirit of the present disclosure. Accordingly, the embodiments disclosed in the present disclosure are provided to describe the technical spirit of the present disclosure, but not intended to limit, and the scope of the technical spirit of the present disclosure is not limited by these embodiments. Therefore, it should be understood that the embodiments described hereinabove are illustrative, but are not limitative, in all aspects. The scope of protection of the present disclosure should be interpreted by the appended claims, and the full technical spirit within the scope in equivalence thereto shall be interpreted as being included in the scope of protection of the present disclosure.

What is claimed is:

1. A neural probe structure comprising:
    a probe having a microfluidic channel, wherein the probe is inserted into an inside of a subject;
    a body to which the probe is fixed, the body having a fluid entrance communicating with the microfluidic channel; and
    a cover element fixed to the body to cover the fluid entrance,
    wherein the cover element comprises a connecting opening to which an external conduit is connected, a plurality of connecting openings to which a plurality of external conduits is connected, a delivery opening placed above and aligned with the fluid entrance, and a fluid delivery channel extending such that the connecting opening and the delivery opening are in fluid communication, and
    a fluid fed from the external conduit flows along the fluid delivery channel, goes into the fluid entrance, and is delivered to the subject through the microfluidic channel, and
    wherein the fluid delivery channel comprises a discharge pipeline extending from the fluid entrance, and a plurality of feed pipelines branching from the discharge pipeline and extending in communication with each of the plurality of connecting openings.

2. The neural probe structure according to claim 1, wherein the feed pipeline is formed to have a curved channel.

3. The neural probe structure according to claim 1, wherein the plurality of feed pipelines has a same cross section perpendicular to a flow direction of the fluid and a same length.

4. The neural probe structure according to claim 1, wherein a plurality of protrusions is formed on an inner wall of the discharge pipeline.

5. The neural probe structure according to claim 1, wherein different fluids are supplied from each of the plurality of external conduits, and a blending ratio of fluids discharged from the probe is adjusted by adjusting an amount of each fluid supplied.

6. The neural probe structure according to claim 1, wherein a width of the delivery opening is smaller than a width of the fluid entrance.

7. The neural probe structure according to claim 1, wherein the fluid delivery channel is formed by covering a groove formed in the cover element with the body.

8. The neural probe structure according to claim 1, wherein the body is made of silicon, and the cover element is made of polydimethylsiloxane (PDMS).

9. The neural probe structure according to claim 8, wherein the body and the cover element are bonded by plasma bonding.

10. The neural probe structure according to claim 1, further comprising:
    a flow rate measuring sensor at an entrance of the microfluidic channel.

11. The neural probe structure according to claim 1, wherein the cover element is configured such that the external conduit is detachably fixed to the cover element.

12. The neural probe structure according to claim 1, wherein the probe has an electrode to measure a neural signal emitted in response to the fluid.

13. The neural probe structure according to claim 1, wherein the probe comprises a probe body having a groove and a wall located in the groove, and a cover glass covering the groove, wherein the microfluidic channel is formed between the probe body and the cover glass according to the groove as the cover glass is supported by the wall.

14. The neural probe structure according to claim 13, wherein the groove of the probe body comprise an anchor groove that is filled with the cover glass when the cover glass is melted, and a channel groove that forms the microfluidic channel between the cover glass and the channel groove.

15. The neural probe structure according to claim 14, wherein the anchor groove is wider than the channel groove.

16. The neural probe structure according to claim 13, wherein the height of the wall is larger than the depth of the groove.

17. The neural probe structure according to claim 13, wherein an outer surface of the cover glass and an outer surface of the probe body where the cover glass is inserted are place on the same plane.

* * * * *